(12) United States Patent
Ballou et al.

(10) Patent No.: US 6,723,118 B1
(45) Date of Patent: *Apr. 20, 2004

(54) FLEXIBLE METAL WIRE STENT

(75) Inventors: Kurt Ballou, Andover, MA (US); George T. Roberts, Mountain Lakes, NJ (US); Kristian J. DiMatteo, Maynard, MA (US); Adrian C. Ravenscroft, Milton, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/587,942

(22) Filed: Jun. 6, 2000

Related U.S. Application Data (63) Continuation of application No. 08/942,162, filed on Oct. 1, 1997, now Pat. No. 6,071,308.

(51) Int. Cl.[7] ................................................. A61F 2/06
(52) U.S. Cl. ...................................... 623/1.15; 623/1.16
(58) Field of Search ............................... 623/1.15, 1.16, 623/1.18, 1.22, 1.17; 606/198

(56) References Cited

U.S. PATENT DOCUMENTS

| | | | |
|---|---|---|---|
| 5,102,417 A | 4/1992 | Palmaz | 606/195 |
| 5,104,404 A | 4/1992 | Wolff | 623/1 |
| 5,135,536 A | 8/1992 | Hillstead | 606/195 |
| 5,195,984 A | 3/1993 | Schatz | 606/195 |
| 5,290,304 A | 3/1994 | Inoue | 606/191 |
| 5,354,308 A | 10/1994 | Simon et al. | 606/198 |
| 5,395,390 A | 3/1995 | Simon et al. | 606/198 |
| 5,421,955 A | 6/1995 | Lau et al. | 216/48 |
| 5,449,373 A | 9/1995 | Pinchasik et al. | 606/198 |
| 5,466,242 A | 11/1995 | Mori | 606/198 |
| 5,514,178 A | 5/1996 | Torchio | 623/12 |
| 5,540,712 A | 7/1996 | Kleshinski et al. | 606/198 |
| 5,545,210 A | 8/1996 | Hess et al. | 623/1 |
| 5,591,197 A * | 1/1997 | Orth et al. | 623/1 |
| D380,266 S | 6/1997 | Boatman et al. | D24/155 |
| D380,831 S | 7/1997 | Kavteladze et al. | D24/155 |
| 5,643,339 A | 7/1997 | Kavteladze et al. | 623/1 |
| 5,649,952 A | 7/1997 | Lam | 606/198 |
| 5,653,727 A | 8/1997 | Wiktor | 606/195 |
| 5,683,411 A | 11/1997 | Kavteladze et al. | 606/200 |
| 5,695,516 A | 12/1997 | Fischell et al. | 606/194 |
| 5,697,971 A | 12/1997 | Fischell et al. | 623/1 |
| 5,702,419 A | 12/1997 | Berry et al. | 606/198 |
| 5,725,572 A | 3/1998 | Lam et al. | 623/1 |
| 5,735,893 A | 4/1998 | Lau et al. | 623/1 |
| 5,800,519 A | 9/1998 | Sandock | 623/1 |
| 5,868,781 A * | 2/1999 | Killion | 62/1.15 |
| 5,879,381 A | 3/1999 | Moriuchi et al. | 623/1 |
| 5,902,332 A | 5/1999 | Schatz | 623/1 |

FOREIGN PATENT DOCUMENTS

| | | |
|---|---|---|
| DE | 40 22 956 A1 | 2/1992 |
| EP | 0 335 341 A1 | 10/1989 |
| EP | 0 421 729 A2 | 4/1991 |
| EP | 0 606 165 A1 | 7/1994 |
| EP | 0 688 545 A1 | 12/1995 |
| WO | WO 9531945 A1 | 1/1995 |
| WO | WO 96/33671 | 10/1996 |

(List continued on next page.)

OTHER PUBLICATIONS

The American Heritage Dictionary of the English Language, p. 1469, 1976.

(List continued on next page.)

*Primary Examiner*—Bruce Snow
(74) *Attorney, Agent, or Firm*—Vidas, Arrett & Steinkraus (57) ABSTRACT

A self-expanding metal wire stent made of shape memory alloy such as nitinol in which a plurality of spaced sections of closed cells are interconnected by straight sections of wire which may be parallel to the longitudinal axis of the stent or may be disposed angularly with respect thereto.

26 Claims, 6 Drawing Sheets

FOREIGN PATENT DOCUMENTS

| WO | WO 96/39102 | 12/1996 |
|---|---|---|
| WO | WO 96/41590 | 12/1996 |
| WO | WO 97/32543 | 9/1997 |
| WO | WO 97/32544 | 9/1997 |
| WO | WO 97/33534 | 9/1997 |
| WO | WO 97/41803 | 11/1997 |
| WO | WO 98/05270 | 1/1998 |
| WO | 98/07386 | 2/1998 |

OTHER PUBLICATIONS

"Percutaneous Endovascular Graft: Experimental Evaluation" by David Lawrence, Jr., M.D., et al, in *Radiology*, May 1987, pp. 357–360.

"Modified Gianturco Expandable Wire Stents In Experimental and Clinical Use" by J. Rosch et al in *CIRSE, Porto Cervo, Sardinia*, May 25–29, 1996.

"Tracheobronchial Tree: Expandable Metallic Stents Used in Experimental and Clinical Applications" by Michael J. Wallace et al, vol. 158, No. 2, RRADIOLOGY, Feb. 1986, pp. 309–312.

"Flexible Balloon–Expanded Stent For Small Vessels" by Gerard Duprat, Jr., et al, RADIOLOGY, Jan. 1987.

"Elastic Characteristics of the Self–Expanding Metallic Stents" by B. G. Fallone, Ph.D., *Investigative Radiology*, May 1988, vol. 23, pp. 370–376.

"Experimental Intrahepatic Portacaval Anastomosis: Use of Expandable Gianturco Stents" by Josef Rosch, M. D., in *RADIOLOGY*, Feb. 1987, pp. 481–485.

"Stenosis of the Vena Cava: Preliminary Assessment of Treatment with Expandable Metallic Stents" by Chusilp Charnsangaveg, M.D. et al in *RADIOLOGY*, vol. 121, No. 2, Feb., 1987, pp. 295–298.

"Expandable Intraluminal Graft: A Preliminary Study" by Julio Palmaz et al, in *RADIOLOGY*, Jul. 1985, pp. 73–77.

"Radiological Follow–Up of Transluminally Inserted Vascular Endoprostheses: An Experimental Study Using Expanding Spirals" by D. Maas et al, *RADIOLOGY*, Sep. 1984, pp. 559–663.

"Gianturco Expandable Wire Stents In the Treatment of Superior Vena Cava Syndrome Recurring After Maximum- –Tolerance Radiation" by Josef Rosch, M.D., et al, in *CANCER*, Sep. 15, 1987, vol. 60, pp. 1239–1246.

*Relocatable Gianturco Expandable Metallic Stents*, by Toshiyuki Irie, MD. et al., *RADIOLOGY*, 1991; 178: 575–578.

PCT Search Report with a date of mailing of Jan. 15, 1999.

* cited by examiner

FLEXIBLE METAL WIRE STENT

CROSS-REFERENCE TO RELATED APPLICATIONS

This application is a Continuation application from Ser. No. 08/942,162 filed Oct. 1, 1997, now U.S. Pat. No. 6,071,308, the entire contents of which are hereby incorporated by reference.

BACKGROUND OF THE INVENTION

This invention relates to stents and is directed more particularly to a self-expanding, generally cylindrical stent preferably made of a shape memory alloy such as Nitinol.

Specifically, it is directed to an improved version of the type of stents described in U.S. Pat. No. 5,354,308 to Simon et al. and U.S. Pat. No. 5,540,712 to Kleshinski et al. The entire contents of these patents is incorporated herein by reference.

The stents of these patents are adapted to assume one configuration in which the stent is expanded and another configuration in which the stent is in a reduced size for delivery by catheter. The stent may be laminated within an elastomeric sleeve.

It has been deemed desirable to provide stents of this kind in elongated versions. Such elongated versions require additional flexibility over the length of the stent.

SUMMARY OF THE INVENTION

It is therefore, an object of the invention to provide stents of the foregoing type in which a plurality of radial sections or segments made up of the cells comprise the body of the stent the segments being interconnected by a single wire or one pair of adjacent sections of the wire which act as bridges, the straight connector sections being longitudinally aligned with the longitudinal dimension of the stent body or at an angle thereto. Such connector sections have been found to provide requisite flexibility in elongated versions of these types of stents both for delivery and implantation.

DETAILED DESCRIPTION OF THE PREFERRED EMBODIMENTS OF THE INVENTION

In the Figures similar numbers are used throughout to indicate similar elements.

Figure 1:
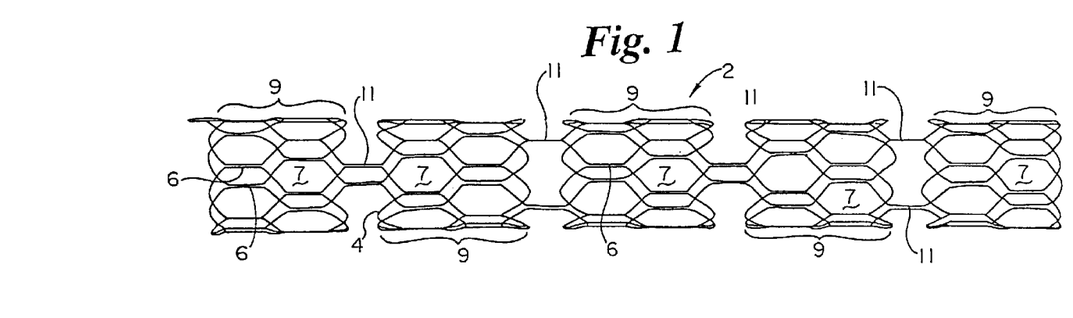
FIG. 1 is a view of one form a stent embodiment of the invention including two bridging sections between cell segments.
Figure 2:
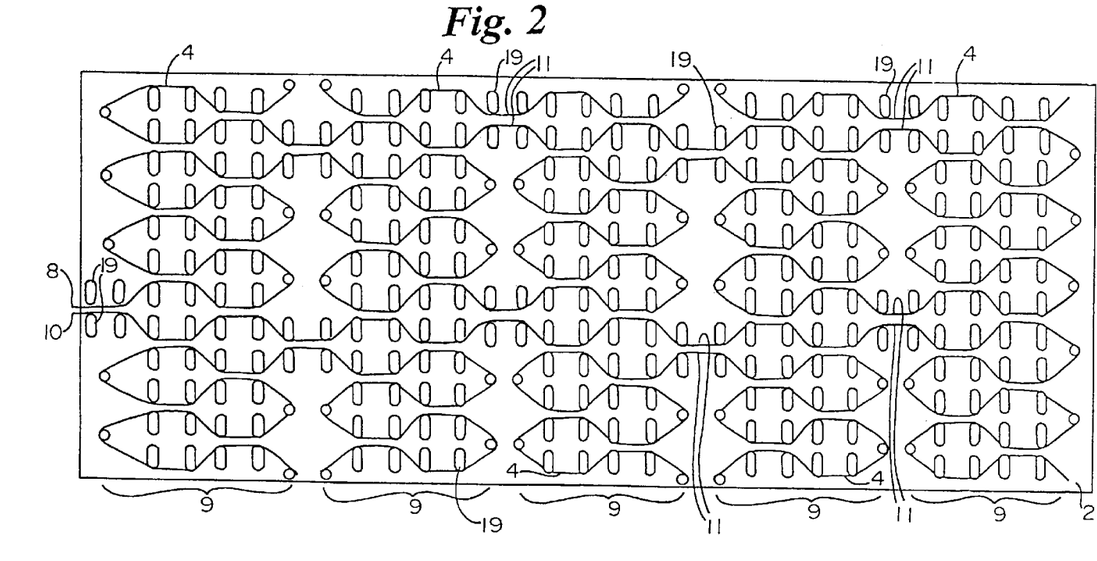
FIG. 2 is a view in flat projection that is a representation in planar view of a mandrel surface with up-standing pins for guiding the placement of a wire (wire winding pattern) in forming a stent of the invention of the type shown in FIG. 1 having two bridging sections between cell segments.
Figure 3:
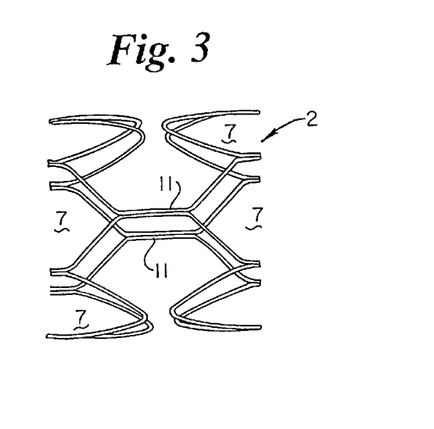
FIG. 3 is a close-up detail view of a portion of the two bridge stent arrangement of FIGS. 1 and 2.

Referring to FIGS. 1–3, it will be seen that one stent embodiment includes a skeletal frame generally indicated at 2, formed from a single wire 4. The frame is in the form of a hollow cylinder as can be seen in the Figures, the front surface being shown in detail while the rear surface is in shadow. Other hollow cross-sectional shapes may be used. The wire 4 includes a plurality of abutting straight portions 6 which are joined to each other, as by welding, to form closed cell configurations 7 which make up spaced sections or cell segments 9 to form the cylindrical body of the stent when connected together by bridging sections 11. In FIGS. 1–3, the stent is shown in a first condition in which the frame is expanded and relatively rigid.

Spaced cell sections or segments 9 are each interconnected by two bridging sections, each consisting of one pair of straight bridging sections 11 of wire 4 which are adjacent to each other and longitudinally aligned with respect to the longitudinal dimension of the stent body portion 9. Straight sections 11 function as connector members to interconnect cell segments 9 and to provide flexibility and spacing therebetween.

FIG. 2 shows the winding pattern of wire 4 in projection on the upstanding pins 19 of cylindrical mandrel 21, also shown in flattened projection. The winding pattern shown provides the desirable stent configuration of FIG. 1 which results in an elongated stent of improved flexibility.

In FIG. 1 the stent is shown in a first condition in which the frame 2 is expanded and substantially tubular in configuration. Ends 8, 10 of the single wire 4 making up the stent are disposed at one end of the stent as can be seen in FIG. 2. These ends are preferably welded together. The abutting and elongated straight portions 6 and 11 of wire 4 facilitate the use of strong elongated welds to securely join wire portions 6 together and 11 together. Preferably, welds of the type disclosed in co-pending U.S. application Ser. No.

08/735,031 will be used for this purpose. The content of that application is incorporated herein by reference. Wire 4 preferably is round in cross-section although it may be square, rectangular, D shape or any other shape. In the straight portions 6 of the frame the joined wire segments are disposed, relative to the tubular configuration of the frame, circumferentially thereof. Wire 4 abuts itself only at the straight portions 6 and 11. It does not cross itself at any point. Accordingly, the frame wall forming the stent has a thickness equal to the diameter of wire 4. The bridging sections or connecting members 11 extend longitudinally with respect to the longitudinal axis of the stent.

The tubular body portion made up of spaced segments 9 comprises a mesh formed by the winding of wire 4, the mesh comprising a plurality of interconnected cells 7 of a polygonal configuration when viewed in plan, providing straight sides to form the aforementioned straight portions 6 and spaced cell segments 9. The polygonal cells 7 preferably are of a hexagonal configuration and are closed, which readily provides expansion and rigidity characteristics desirable in the structure and operation of the stent. Preferably, the stent comprises 6 of the polygonal cells 7 circumferentially and an even number of the polygonal cells along its length, thereby facilitating formation of the stent by the single wire 4 in the pattern shown in FIG. 2.

The stents of this invention may have disposed thereon an elastomeric or textile sleeve (not shown) such as PET, PTFE, silk, polyurethanes or polyesters for example, which is expandable on the stent as the stent expands to its enlarged configuration. The sleeves may include drugs. The sleeved stent may have added benefit in certain circumstances and thus is considered to be within the scope of the present invention.

The stent wire is preferably made of an alloy of nickel and titanium which provides the stent with a thermal memory. The unique characteristics of such alloys which are generally known as "Nitinol" is that they have thermally triggered shape memories which allows the stent to be constructed in the aforesaid first condition, i.e., expanded and the alloy to be cooled and thereby softened compressing to a second condition, i.e., smaller for loading into a catheter in a relatively compressed state and to regain the memorized enlarged shape when warmed to a selected temperature such as human body temperature. The two interchangeable shapes sizes are possible because of the two different crystalline structures which exist in such alloys at different temperatures.

Accordingly, as is known in the art, when stents of the type described herein are subjected to a temperature at or less than the transition temperature of the alloy, the relatively rigid stent changes to a second condition in which it is relatively compressible. In such a condition the stent may be compressed easily to a small diameter which is conveniently delivered by means of a catheter for implanting. The stent following implantation upon reaching a higher temperature such as body temperature then self-expands to its memorized larger shape.

Of course, the stents of this invention may be made of other materials such as stainless steel to be balloon expandable or the like as known in the art. Polymeric materials may also be used. Composites of Nitinol with other metals such as chrome or nitinol cored wire cored with alloys such as tantalum may be used.

Figure 4:
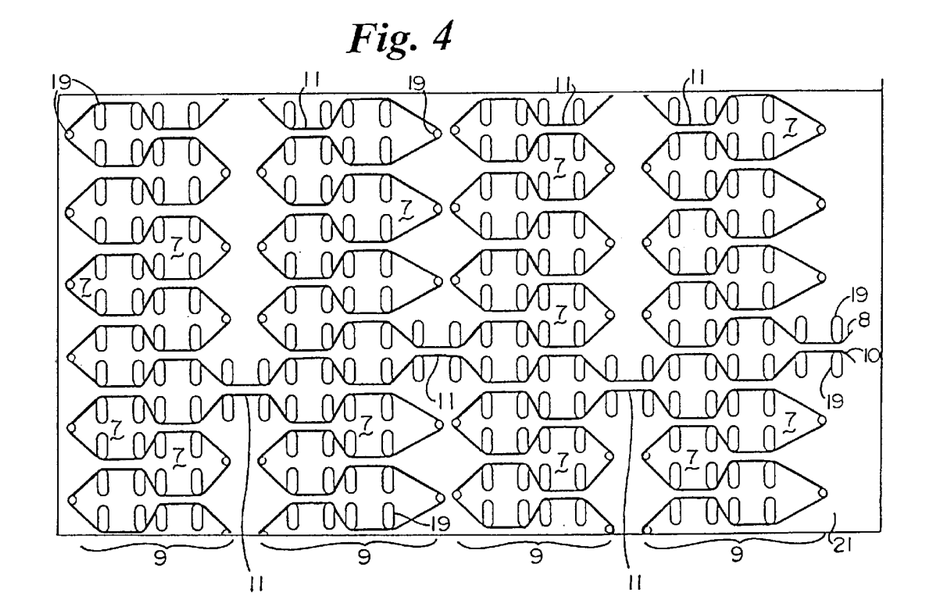
FIG. 4 is a planar view similar to FIG. 2 showing the wire winding patterns for preparing a stent embodiment having a single bridge section between stent segments, the bridge section being parallel to the longitudinal axis of the stent.

FIG. 4 shows the winding pattern for forming a stent similar to that of FIGS. 1–3 but having only one bridging section or connecting member 11 between cell segments 9. Only a single wire is used in this wire winding pattern and the connecting members are parallel to the longitudinal axis of the stent.

Figure 5:
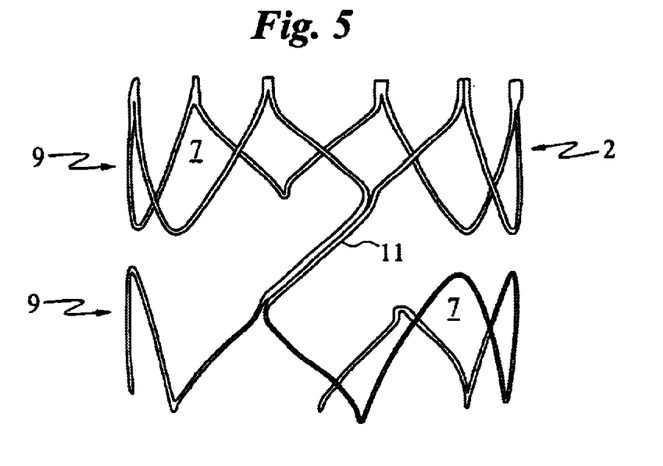
FIG. 5 is a close-up detail view of a portion of a stent embodiment having a single bridge section between stent segments, the bridging sections being at an angle with respect to the longitudinal axis of the stent.
Figure 6:
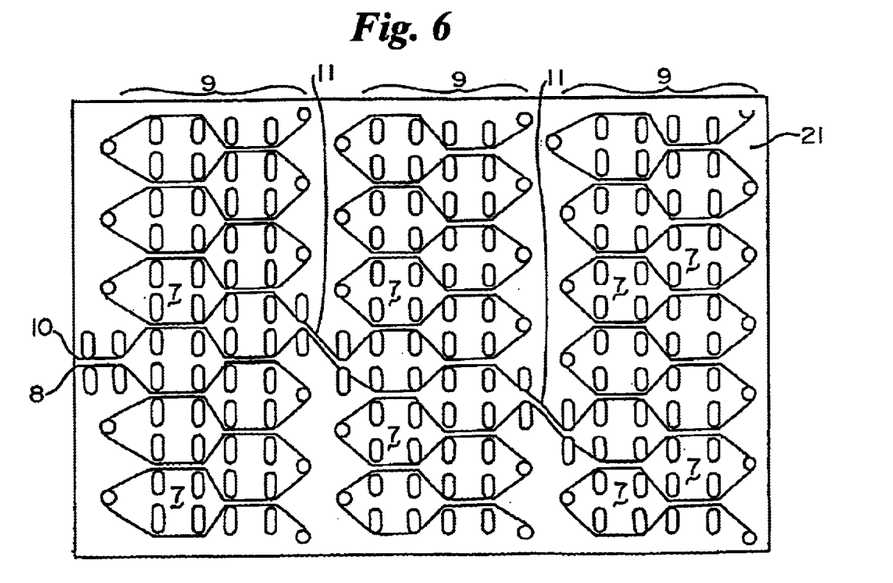
FIG. 6 is a planar view similar to FIGS. 2 and 4 showing the wire winding pattern for preparing a stent embodiment as shown in FIG. 5.

FIGS. 5 and 6 shown an embodiment 2 in which the single connecting member 11 between adjacent segments 9 is angularly positioned with respect to the longitudinal axis of the stent. FIG. 5 shows a portion of the stent including the single angled connector between stent segments. FIG. 6 is the winding pattern for this embodiment.

Figure 7:
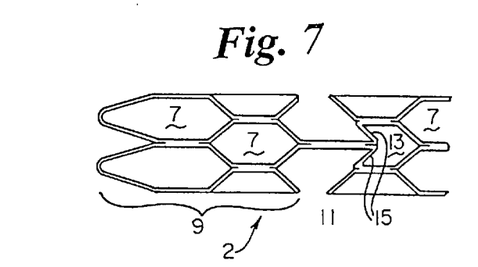
FIG. 7 is a modified showing of a single bridge arrangement for minimizing shortening of the stent during compression.

FIG. 7 shows another alternative stent design 2 with a single bridge connector member 11. It consists of a single wire multiple segment hexagonal cell stent having the ability to provide minimal shortening in overall length during compression to a smaller diameter for delivery. In this design the wire configuration of hexagonal shaped cells 7 emanating from segment 9 join a hexagonal cell 13 having a reverse direction 15 for two sides of the cell to allow the cell to absorb the opposite cell's elongation. This inversion is only necessary at the junction points of connector member connections of the segments. The inversion arrangement may be used with other cell geometric shapes.

Figure 8:
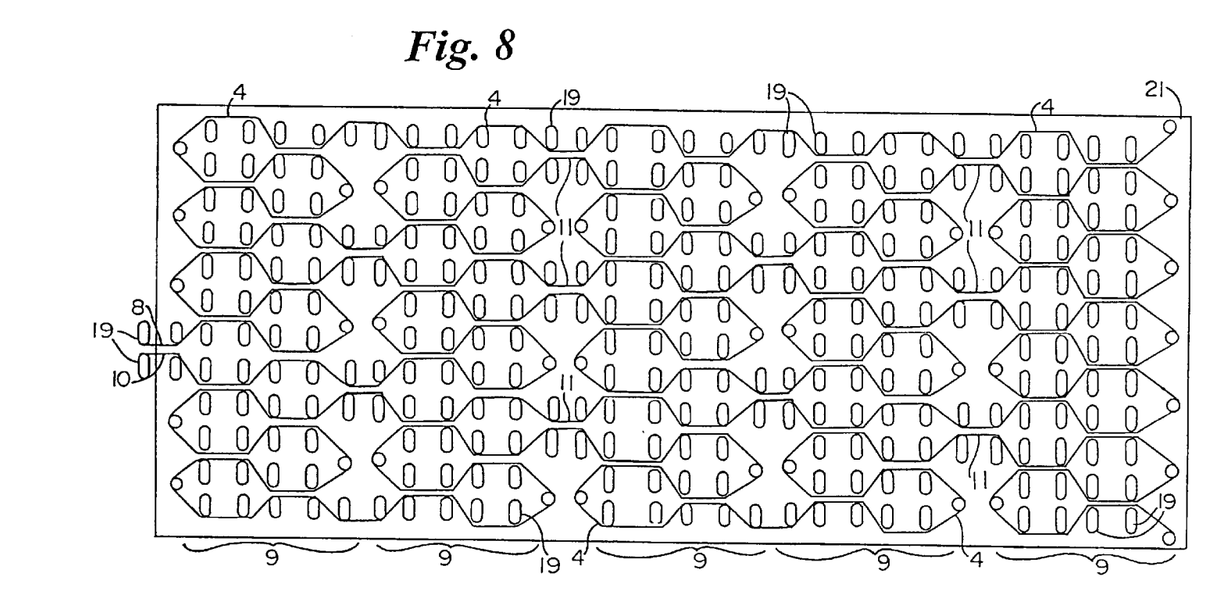
FIG. 8 is a planar view similar to FIGS. 2, 4 and 6 showing the wire winding pattern for preparing a stent having three bridging sections between cell segments.

Referring now to FIG. 8, the wire winding pattern for preparing a stent having three bridge connector members 11 between each of segments 9 is shown. The same members are used to indicate elements which are similar to those of FIGS. 2 and 4.

Figure 9:
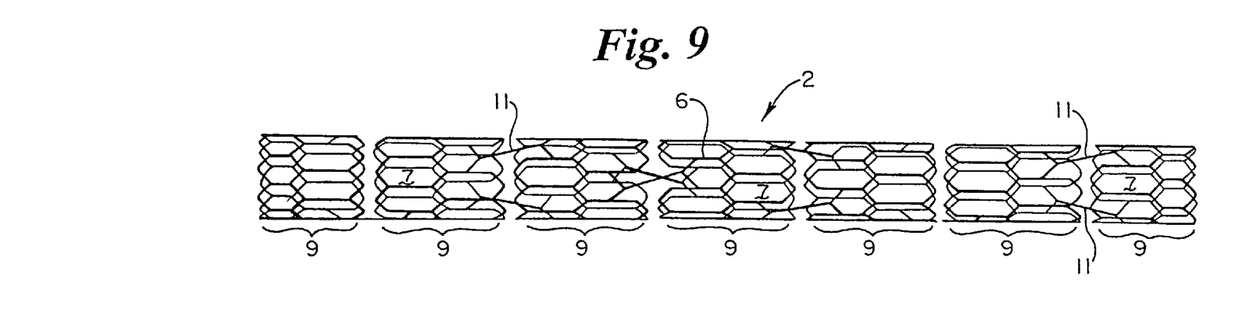
FIG. 9 is a view of an embodiment of a stent having two bridging sections between cell segments, the sections being angularly positioned with respect to each other and with respect to the longitudinal axis of the stent.
Figure 10:
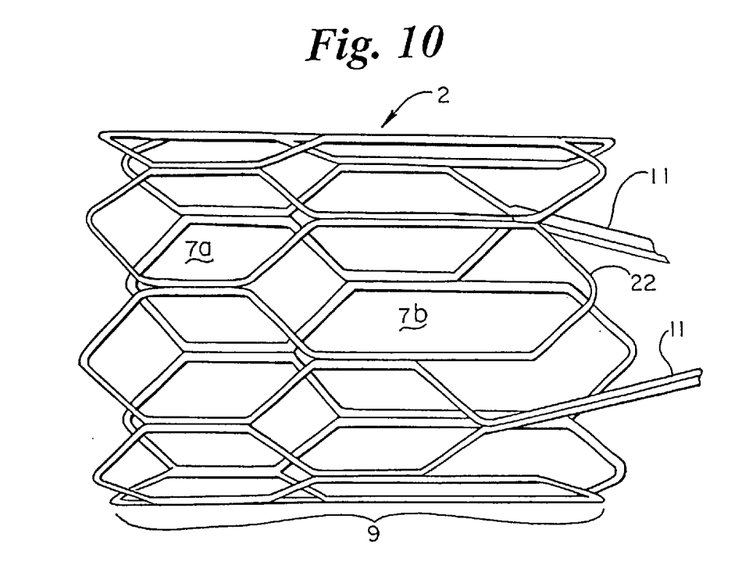
FIG. 10 is a close-up detail view of a portion of the two bridge stent arrangement of FIG. 9 wherein the cell segments are off set with respect to adjacent segments and the bridging sections are at an angle with respect to the longitudinal axis of the stent.
Figure 11:
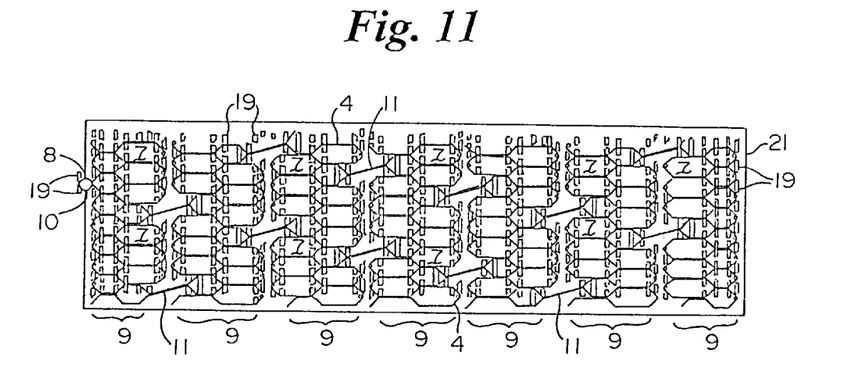
FIG. 11 is a planar view similar to FIGS. 2, 4, 6 and 8 showing the wire winding pattern for preparing the stent of FIGS. 9 and 10.

Another particularly preferred embodiment is shown in FIGS. 9, 10 and 11 wherein the bridging connector members 11 are two in number between segments 9 and are angularly positioned with respect to each other and with respect to the longitudinal axis of the stent. The various size cells 7a and 7b making up each of the cell segments 9, the segments being offset with respect to each other such that the adjacent points 22 of the segments do not contact each other when the stent is bent as in flexing it to move around bends in the vasculature. The same numbers are used to indicate elements similar to those of FIG. 1. FIG. 10 shows a close-up detail of the connectors 11 in a portion of the stent shown in FIG. 9. FIG. 11, similar to FIGS. 2, 4, 6 and 8, show the wire winding pattern to be used in preparing the stent.

Figure 12:
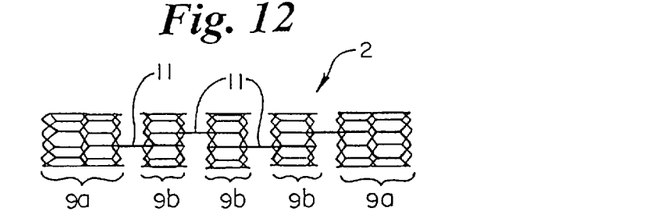
FIG. 12 is a view of another stent embodiment having bridging sections extending between adjacent segments of the stent, successive bridging sections being displaced or staggered circumferentially with respect to each other.
Figures 13, 14:
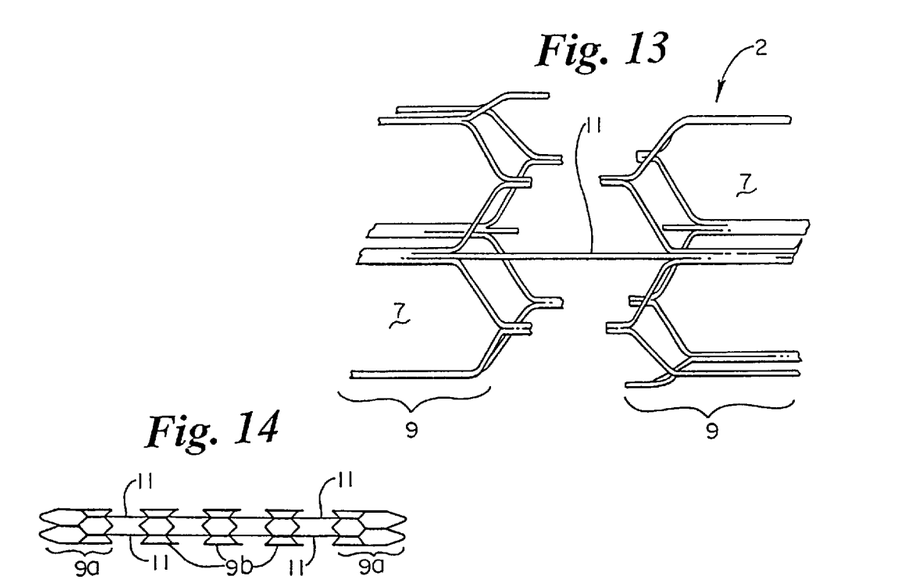
FIG. 13 is a close-up detail view of a portion of the stent of FIG. 12.
FIG. 14 is a showing of a stent similar to that of FIGS. 12 and 13 except that the bridging sections (two) extend continuously through the length of the stent.

The embodiment of FIGS. 12 and 13 differs of the preceding embodiments in that a plurality of wires are used to form the stent. In this embodiment each segment 9 is formed of a individual wire, the end segments 9a being two cells in length while the internal segments 9b are only one cell in length. Connector members 11 extend between adjacent segments 9 and are interconnected as shown in the Figures. This embodiment includes a staggered single wire bridge arrangement between segments.

The embodiment of FIG. 14 is similar in most respects to that of FIGS. 12 and 13 except that connector member 11 extends continuously through the longitudinal length of the stent. The two connector members 11 are connected substantially 180° apart. Optionally, only one continuous connector member may be included.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent comprised of a tube form body having a body wall structure of a geometric pattern of cells, the cells being substantially in the shape of a convex polygon, and defining a cell pattern as a plurality of spaced sections of interconnected cells defined by wire extending throughout the body, one or more of the plurality of adjacent spaced sections being defined by at least two rows of cells circumferentially distributed about the tube, adjacent spaced sections being connected to each other by at least one straight connector section of the wire, the at least one straight connector section having a first end and a second end, wherein the first end is in direct contact with one of the adjacent spaced sections and the second end is in direct contact with one of the adjacent spaced sections and wherein the at least one straight connector section is substantially straight between the first end and the second end, at least one cell of each of the adjacent spaced sections being unconnected to the adjacent spaced section.

2. The stent of claim 1 wherein the cells are of a hexagonal configuration.

3. The stent of claim 2 wherein at least some of the cells include two adjacent inverted sides which receive the at least one straight connector section.

4. The stent of claim 1 wherein the at least one straight connector section comprises two connector sections, the two connector sections being circumferentially spaced apart by about 180 degrees.

5. The stent of claim 1 wherein the at least one straight connector section comprises three connector sections, the three connector sections being circumferentially spaced apart by about 120 degrees.

6. The stent of claim 1 wherein at least a portion of the stent is constructed from nitinol alloy.

7. The stent of claim 1 further comprising a covering sleeve.

8. The stent of claim 1 wherein the at least one straight connector section of the wire comprise at least one continuous wire extending throughout the longitudinal length of the stent.

9. The stent of claim 8 wherein the at least one continuous wire comprises a plurality of wires.

10. The stent of claim 1 wherein the tube form body is constructed from a single wire.

11. The stent of claim 1, wherein the cells have no more than six internal angles.

12. The stent of claim 1, wherein there is no more than three straight connector sections between each pair of adjacent spaced section.

13. The stent of claim 1, the at least one straight connector section being disposed at an oblique angle relative to the longitudinal axis of the stent.

14. A stent comprised of a tube form body having a body wall structure of a geometric pattern of cells and defining a cell pattern as a plurality of spaced sections of interconnected cells defined by wire extending throughout the body, one or more of the plurality of adjacent spaced sections being defined by at least two rows of cells circumferentially distributed about the tube, adjacent spaced sections being connected to each other by at least one straight connector section of the wire, the at least one straight connector section having a first end and a second end, wherein the first end is in direct contact with one of the adjacent spaced sections and the second end is in direct contact with one of the adjacent spaced sections and wherein the at least one straight connector section is substantially straight between the first end and the second end, wherein there are a plurality of cells separating each adjacent straight connector sections, at least one cell of each of the adjacent spaced sections being unconnected to the adjacent spaced section, and further wherein the at least one straight connector section being disposed at an oblique angle relative to the longitudinal axis of the stent.

15. The stent of claim 14, wherein there is no more than three straight connector sections between each pair of adjacent spaced section.

16. The stent of claim 14, wherein the cells are in the shape of a convex polygon.

17. The stent of claim 14, wherein the cells are of a hexagonal configuration.

18. The stent of claim 14 wherein at least a portion of the stent is constructed from nitinol alloy.

19. The stent of claim 14 wherein the tube form body is constructed from a single wire.

20. A stent comprised of a tube form body having a body wall structure of a geometric pattern of cells and defining a cell pattern as a plurality of spaced sections of interconnected cells defined by wire extending throughout the body, one or more of the plurality of adjacent spaced sections being defined by at least two rows of cells circumferentially distributed about the tube, adjacent spaced sections being connected to each other by at least one straight connector section of the wire, the at least one straight connector section having a first end and a second end, wherein the first end is in direct contact with one of the adjacent spaced sections and the second end is in direct contact with one of the adjacent spaced sections and wherein the at least one straight connector section is substantially straight between the first end and the second end, the at least one straight connector section being disposed at an oblique angle relative to the longitudinal axis of the stent, wherein the cells are formed of a plurality of substantially straight segments, at least one cell of each of the adjacent spaced sections being unconnected to the adjacent spaced section, wherein the at least one straight connector section is comprised of at least one pair of adjoining wire segments.

21. The stent of claim 20, the at least one straight connector section being disposed at an oblique angle relative to the longitudinal axis of the stent.

22. The stent of claim 20, wherein there is no more than three straight connector sections between each pair of adjacent spaced section.

23. The stent of claim 20, wherein the cells are in the shape of a convex polygon.

24. The stent of claim 20, wherein the cells are of a hexagonal configuration.

25. The stent of claim 20 wherein at least a portion of the stent is constructed from nitinol alloy.

26. The stent of claim 20 wherein the tube form body is constructed from a single wire.

* * * * *